US009808269B2

United States Patent
Budiman et al.

(10) Patent No.: US 9,808,269 B2
(45) Date of Patent: Nov. 7, 2017

(54) ADJUSTABLE MEDICAL RETRIEVAL DEVICES AND RELATED METHODS OF USE

(71) Applicant: Boston Scientific Scimed, Inc., Maple Grove, MN (US)

(72) Inventors: Tantra S. Budiman, Newton, MA (US); Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 103 days.

(21) Appl. No.: 14/565,859

(22) Filed: Dec. 10, 2014

(65) Prior Publication Data

US 2015/0164522 A1    Jun. 18, 2015

Related U.S. Application Data

(60) Provisional application No. 61/915,352, filed on Dec. 12, 2013.

(51) Int. Cl.
*A61B 17/221*    (2006.01)

(52) U.S. Cl.
CPC .... *A61B 17/221* (2013.01); *A61B 2017/2212* (2013.01)

(58) Field of Classification Search
CPC .......... A61B 17/221; A61B 2017/2215; A61B 2017/2212; A61B 2017/2217
See application file for complete search history.

(56) References Cited

U.S. PATENT DOCUMENTS

| | | | | |
|---|---|---|---|---|
| 4,326,530 A * | 4/1982 | Fleury, Jr. | ........ | A61B 17/32056 606/47 |
| 4,718,419 A * | 1/1988 | Okada | .............. | A61B 17/32056 606/39 |
| 5,163,942 A * | 11/1992 | Rydell | ............. | A61B 17/32056 606/1 |
| 5,613,973 A * | 3/1997 | Jackson | ............. | A61B 17/0218 606/1 |
| 5,906,622 A | 5/1999 | Lippitt et al. | | |
| 5,924,175 A | 7/1999 | Lippitt et al. | | |
| 6,146,396 A * | 11/2000 | Konya | ................. | A61B 17/221 606/159 |

(Continued)

*Primary Examiner* — Alexander Orkin
(74) *Attorney, Agent, or Firm* — Bookoff McAndrews, PLLC (57) ABSTRACT

A medical device may include a distal end having an expandable grasping portion with a plurality of movable branch members, and at least one filament connected to and slidably movable within at least a portion of the plurality of movable branch members. The proximal end of the device may include a handle having an actuation guide and an actuation selector connected to and movable along the actuation guide. The actuation selector may be coupled to ends of the at least one filament and may be configured to exert a force on the filament to vary the size of the grasping portion between a plurality of pre-selected discrete configurations of the grasping portion. In addition, the medical device may include a sheath member extending from the distal end toward the proximal end. The proximal ends of the plurality of movable branch members may be disposed within the sheath member.

14 Claims, 6 Drawing Sheets

(56) References Cited

U.S. PATENT DOCUMENTS

| | | | |
|---|---|---|---|
| 6,168,603 B1 * | 1/2001 | Leslie | A61B 17/221 606/114 |
| 6,174,318 B1 | 1/2001 | Bates et al. | |
| 6,626,915 B2 | 9/2003 | Leveillee et al. | |
| 6,652,537 B2 * | 11/2003 | Mercereau | A61B 17/221 606/113 |
| 6,743,228 B2 * | 6/2004 | Lee | A61B 8/0825 606/113 |
| 7,041,108 B2 | 5/2006 | Lippitt et al. | |
| 7,210,210 B2 | 5/2007 | Lippitt et al. | |
| 7,322,989 B2 | 1/2008 | Teague et al. | |
| 2002/0095161 A1 * | 7/2002 | Dhindsa | A61B 17/221 606/120 |
| 2004/0215212 A1 * | 10/2004 | Teague | A61B 17/221 606/127 |
| 2007/0106304 A1 * | 5/2007 | Hammack | A61B 17/221 606/113 |
| 2008/0039684 A1 * | 2/2008 | Clayman | A61B 1/018 600/104 |

* cited by examiner

ADJUSTABLE MEDICAL RETRIEVAL DEVICES AND RELATED METHODS OF USE

This application claims the benefit of U.S. Provisional Application No. 61/915,352, filed Dec. 12, 2013, the disclosure of which is incorporated herein by reference in its entirety.

TECHNICAL FIELD

The present disclosure relates generally to medical retrieval devices and related systems and methods. More specifically, the present disclosure relates to adjustable medical retrieval devices, systems, and methods for retrieving matter within a patient.

BACKGROUND

Medical retrieval devices are often utilized for removing organic material (e.g., blood clots, tissue, and biological concretions such as urinary, biliary, and pancreatic stones) and inorganic material (e.g., components of a medical device or other foreign matter), which may obstruct or otherwise be present within a patient's body cavities. For example, concretions can develop in certain parts of the body, such as in the kidneys, pancreas, and gallbladder. Minimally invasive medical procedures are used to remove these concretions through natural orifices, or through an incision, such as during a percutaneous nephrolithotomy (PNCL) procedure. Further, lithotripsy and ureteroscopy, for example, are used to treat urinary calculi (e.g., kidney stones) in the ureter of a patient.

Further, known medical retrieval devices are complex in structure, requiring many components and labor-intensive manufacturing processes, and many do not provide controls for varying the size of the retrieval end of the device. The assembly of small parts often requires visual magnification and specialized training. The joining mechanisms often increase the profile of the medical retrieval devices beyond optimal design parameters, and are often the weakest structural points. These drawbacks result in medical retrieval devices that may be bulky, expensive, and prone to failure.

Thus, there remains a need for improved medical devices having reduced profiles, adjustable sizes, and fewer components for use in retrieving, moving, and gauging body matter.

SUMMARY OF THE DISCLOSURE

In accordance with an embodiment, the present disclosure is directed to a medical device including a distal end with an expandable grasping portion. The grasping portion may include a plurality of movable branch members having a lumen, and at least one filament connected to and slidably movable within at least a portion of the plurality of movable branch members. The device also may include a proximal end with a handle having an actuation guide and an actuation selector connected to and movable along the actuation guide. The actuation selector may be coupled to ends of the filament and may be configured to exert a force on the filament to vary the size of the grasping portion between a plurality of pre-selected discrete configurations of the grasping portion. In addition, the device may include a sheath member extending from the distal end toward the proximal end. The proximal ends of the plurality of branch members may be disposed within the sheath member.

One or more embodiments may include one or more of the following features: the at least one filament may comprise a single filament having portions extending through the lumen of each of the plurality of branch members and couple to the actuation selector; the at least one filament comprises a first and second filament, the first filament extends through the lumen of a first set of branch members and is coupled to the actuation selector, and the second filament extends through the lumen of a second set of branch members and is coupled to the actuation selector; each of the plurality of branch members may be pre-bent to extend radially from a longitudinal axis when a force is not applied to the plurality of movable branch members; a distal portion of each of the plurality of movable branch members may have linear neutral position when a force is not applied to the plurality of movable branch members; distal portions of the at least one filament may extend from the distal apertures of the plurality of movable branch members and intersect at an apex; the distal portions of the at least one filament intersecting at the apex may be connected to each other; the distal portions of the at least one filament intersecting at the apex and connected to each other may be connected via a knot; the actuation selector may be coupled to each of the ends of the at least one filament via a drive-wire; the force exerted by the actuation selector on the at least one filament may extend or retract the at least one filament from distal apertures of the plurality of movable branch members; the actuation guide may include d notches corresponding to the discrete configurations of the grasping portion; the notches may further correspond to a pre-determined length of the filament to be retracted or extended; the notches may be labeled.

In accordance with another embodiment, the present disclosure is directed to a medical device, including a distal end including an expandable grasping portion having a plurality of movable branch members having a lumen, and at least two filaments each connected to and slidably movable within at least a portion of the plurality of movable branch members. The device may include a proximal end with a handle having an actuation guide and an actuation selector connected and movable along the actuation guide. The actuation selector may be coupled to each end of the two or more filaments and may be configured to exert a force on the two or more filaments to vary the size of the grasping portion between a plurality of pre-selected discrete configurations of the grasping portion. The device may include a sheath member extending from the distal end toward the proximal end. The proximal ends of the plurality of branch members may be disposed within the sheath member.

In accordance with another embodiment, the present disclosure may be directed to a medical device having a distal end with an expandable grasping portion having a plurality of movable branch members having a lumen, and at least one filament connected to and slidably movable within at least a portion of the plurality of movable branch members. The device may include a proximal end including a handle having an actuation guide and at least two actuation selectors connected to and movable along the actuation guide. The at least two actuation selectors may be coupled to ends of the at least one filament and may be configured to exert a force on the at least one filament to vary the size of the grasping portion between a plurality of pre-selected discrete configurations of the grasping portion. In addition, the device may include a sheath member extending from the distal end toward the proximal end. The proximal ends of the branch members may be disposed within the sheath member.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts.

Figure 1:
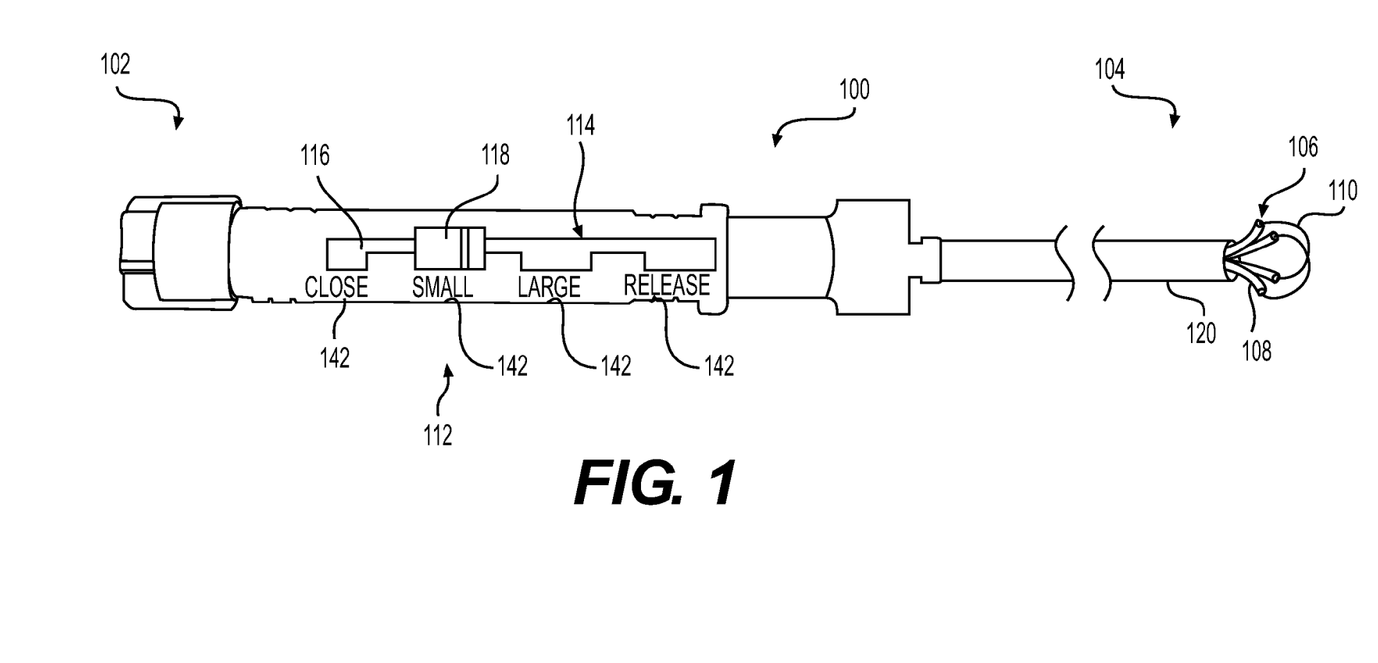
FIG. 1 is a side view illustration of a medical retrieval device in accordance with an embodiment of the present disclosure.

As shown in FIG. 1, a medical retrieval device 100 according to an exemplary embodiment of the present disclosure may extend from a proximal end 102 closest to a user, to a distal end 104, closest to a patient target site. The device 100 may include an expandable grasping portion 106 at the distal end 104, and a handle 112 at the proximal end 102 having an actuator 114. The actuator 114 may include an actuation guide 116 having one or more identifiers 142 corresponding to various predetermined or pre-selected discrete configurations of the grasping portion 106 and an actuation selector 118 configured to move along the actuation guide 116. The device 100 also may include a sheath member 120 disposed between the proximal and distal ends 102 and 104.

The distal end 104 of the device may be configured for insertion into the body and the handle 112 may be configured to be held by the user (e.g. medical doctor, medical professional) and used to manipulate the grasping portion 106, via the actuator 114 of the handle 112. The grasping portion 106 may include a plurality of movable branch members 108 and portions of a filament 110. Portions of the filament 110 may extend from the distal ends of the branch members 108 and may be configured into a basket to gather body matter. The gathered body matter may be retained by the branch members 108.

Figure 2:
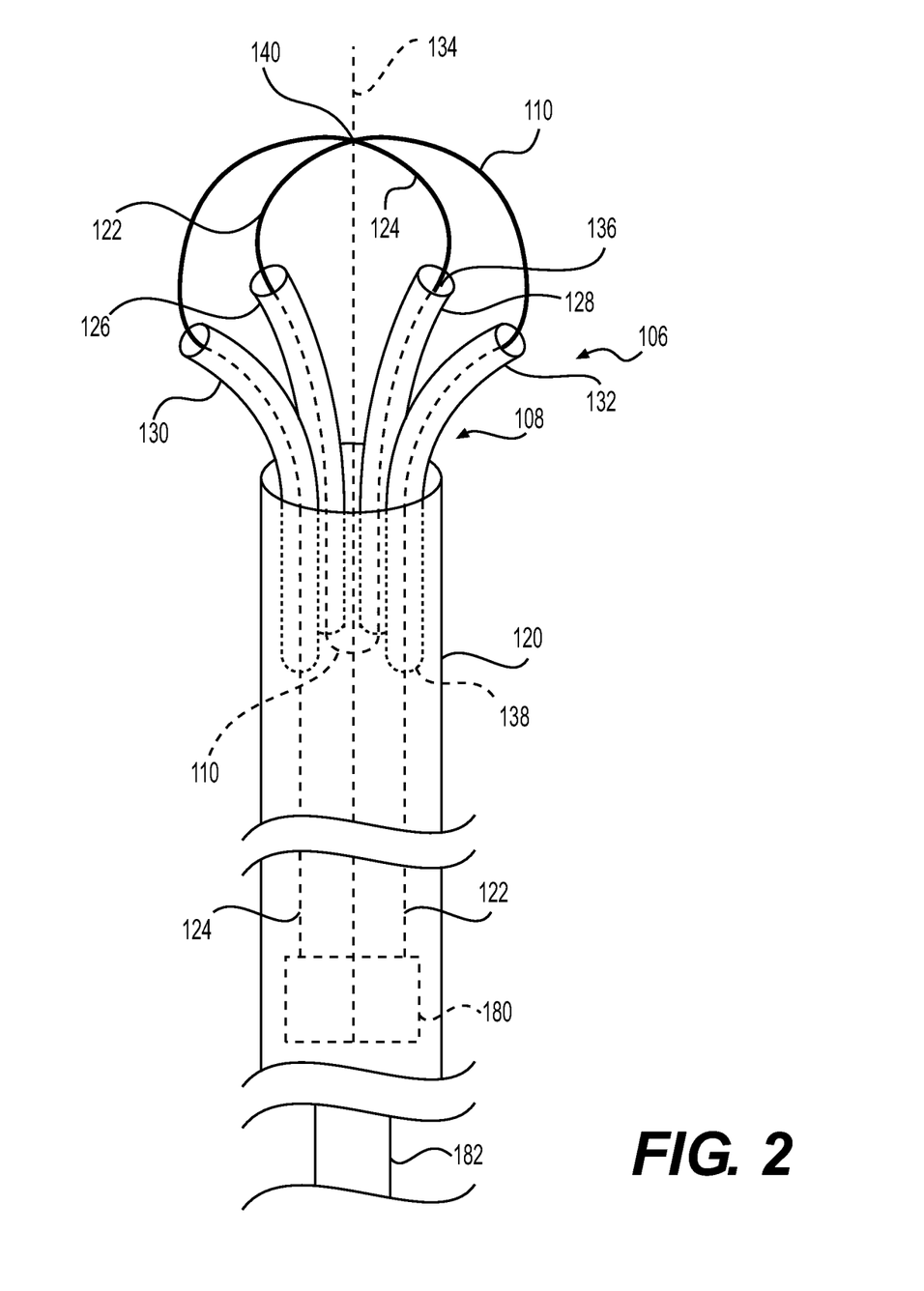
FIG. 2 is a partial side view illustration of a distal portion of the medical retrieval device of FIG. 1 in an expanded configuration.

FIG. 2 illustrates the grasping portion 106 at the distal end 104 of the device 100 in further detail. As shown in FIG. 2, the grasping portion 106 is in an expanded configuration and includes the branch members 108 and portions of the filament 110. Specifically, FIG. 2 shows four movable branch members 126, 128, 130 and 132 (collectively referred to by reference numeral 108). In the expanded configuration shown in FIG. 2, distal portions of the branch members 108 may be disposed radially outward from a longitudinal axis 134 and proximal portions of the branch members 108 may be disposed in the sheath member 120. Distal portions of the branch members 108 may be connected to portions of the filament 110, in any suitable manner, to form the grasping portion 106. In a non-expanded configuration, (see FIG. 3) the distal portions of the branch members 108 may be arranged in any suitable manner, and may be movable from radially extended positions to substantially linear positions. For example, in the embodiment shown in FIGS. 1 and 2 the distal ends of the four movable branch members 126, 128, 130, and 132 may be movable and extended away from the longitudinal axis 134. However, it should be noted that any other suitable number of branch members 108 and/or arrangement may alternatively be utilized.

Portions of the branch members 108 may be formed or pre-bent to extend radially from the longitudinal axis 134 in a neutral, non-forced configuration. If pre-bent or curved, the branch members 108 may each have their own orientation or the same as any other branch member 108.

Alternatively, branch members 108 may be formed to have a substantially linear neutral position and may be forced to extend radially from the longitudinal axis 134. Proximal portions of the branch members 108 may be parallel, stationary, and adjacent and may be disposed within one or more of the sheath members 120, such as a heat shrink member. Proximal portions of the branch members 108 disposed within the sheath member 120 may be connected together in any suitable manner adjacent a distal end of the sheath member 120 and may terminate adjacent the distal end of the sheath member 120. The sheath member 120 may be attached to the branch members 108 in any suitable manner, such as by glue, heat bond, heat shrinking, molding, or by any mechanical attachment.

In some embodiments, the branch members 108 may be substantially similar, and each may be formed in a tubular shape having a lumen. The branch members 108 also may have any geometric profile so that they may have a low profile when collapsed, such as a flat surface to flat surface and one or more branch members 108 may fit into another branch member 108.

The branch members 108 may be formed using any suitable materials. In one embodiment, the branch members 108 may be manufactured using one or more than one co-axial polymer tubes, such as, e.g., polyimide, and polyethylene terephthalate (PET), among others. The branch members 108 may have any suitable circumferential wall thickness and internal diameter. In one example, a branch member 108 may have a wall thickness of about 0.0004 inches, and an internal diameter (ID) of about 0.005 inches, though any other suitable wall thickness and internal diameter suitable for use in the body may alternatively be utilized. Branch members 108 may have a small lumen for the filament and relatively thick walls and/or may have a large lumen and relatively thin walls or any other suitable arrangement.

One or more of the branch members 108 may be replaced with a stationary heat shrink member having a diameter smaller than the branch members, thereby further reducing the overall diameter of the sheath 120. For example, two of the four branch members (e.g. 126 and 128) shown in FIG. 2 may be formed of a heat shrink material and rigidly connected to portions of the filament 110 and the sheath member 120. In this example, portions of the filament 110 may be fixed along one or more portions of the stationary branch members 126 and 128, e.g. via a heat shrinking. In this example, the branch members 126 and 128 may have a smaller diameter than the other branch members 130 and 132 through which the filament 110 moves.

The branch members 108 may each include distal apertures 136 and proximal apertures 138, which provide the filament 110 access into and out of the branch members 108. The apertures 136 and 138 may have any suitable size, shape, or geometry and may be formed by any suitable method, such as laser cutting or mechanical cutting, or may be formed during the manufacture of the branch members 108, such as rolling a flat material to form the branch members 108 with openings at either end.

The filament 110 may be formed using any suitable material. Such suitable materials may include, but are not limited to, metals, polymers, or a combination of materials, having suitable flexibility, strength, and/or stiffness to move the branch members 108 between expanded and closed configurations. In one embodiment, one or more portions of the filament 110 may be formed using a metal wire, such as nitinol. Portions or the entire length of the filament 110 may be coated with a polymer. In an alternative example, the filament 110 may be formed from two or more metals that are co-drawn together. In another embodiment, the filament 110 may be a suture. The filament 110 may have properties including: elasticity, columnar strength, and flexibility, and may include various coatings, such as a friction coating and/or therapeutic coatings. The filament 110 may have any suitable size and cross-sectional profile e.g., circular, rectangular, oval, or polygonal. In some embodiments, portions of the filament 110 may be flattened, machined, extruded, drawn, or etched into a different profile than a remaining portion of the filament 110. In some embodiments, portions of the filament 110 may be slotted or pre-bent to allow deflection or directional bending. In one embodiment, the filament 110 may be formed with a super elastic material or a shape memory material, such as, e.g., nitinol wires having any suitable diameter (e.g. 0.003 inches). All or portions of the exterior surfaces of the branch members 108 and/or the filament 110 may be roughened, notched, etched, sand-blasted, or otherwise modified to provide a better gripping surface, and may include any additional features such as hooks, barbs or coated gripping sections.

As discussed above, the grasping portion 106 at the distal end 104 of the device 100 may form a basket configuration by connecting portions of the filament 110 to the branch members 108. The following is an example of such a connection configuration as shown in FIG. 2. One end 122 of the filament 110 may be inserted through the proximal aperture 138 of the first branch member 126, up through the lumen of the first branch member 126 and out of the distal aperture 136 of the first branch member 126. Similarly, the other end 124 of the filament 110 may be inserted through the proximal aperture 138 of a second branch member 128 that is adjacent the first branch member 126, up through the lumen of the second branch member 128 and out of the distal aperture 136 of the second branch member 128. The end 122 of the filament 110 exiting the distal aperture 136 of the first branch member 126 may be inserted or threaded through the distal aperture 136 of a third branch member 130, through the lumen of the third branch member 130, out of the proximal aperture 138 of the third branch member 130 and may be operatively coupled to the actuation selector 118 via, for example, a drive wire 182 or any other suitable manner.

Similarly, the end 124 of the filament 110 exiting the distal aperture 136 of the second branch member 128 may then be inserted or threaded through the distal aperture 136 of the fourth branch member 132, through the lumen of the fourth branch member 132, out of the proximal aperture 138 of the fourth branch member 132 and may be attached either directly to the actuation selector 118 via, for example, a drive wire 182 or any other suitable manner. As used herein, the term "coupled" refers to directly or indirectly coupled.

In one embodiment, each end of the filament 122 and 124 may be coupled to the drive wire 182 via a connector 180, such as a crimp, bending the filament or wire, tying the filament or wire or any other suitable manner. The wire may be manufactured using any suitable material, such as a metal, or polymer having suitable properties to transfer forces from the actuator and may have any suitable dimensions.

The portions of the filament 110 extending out of the distal apertures 136 of the branch members 110 may intersect or cross at an apex 140. The apex 140 may be positioned along the longitudinal axis 134 of the grasping portion 106. The portions of the filament 110 that intersect at the apex 140 may be connected in any suitable manner. Examples of such connections may include: knots, glue, solder, twisting, etc. Alternatively, the intersection portions of the filament 110 may not be connected, and each portion of the filament 110 may move or flex independently, and these independently movable portions of the filament 110 may contact portions of the body to capture and/or assist in treating body matter. Portions of the filament 110 extending from the distal apertures 136 of the branch members 108 may form a basket having side openings through which body matter may enter.

Figures 3, 4:
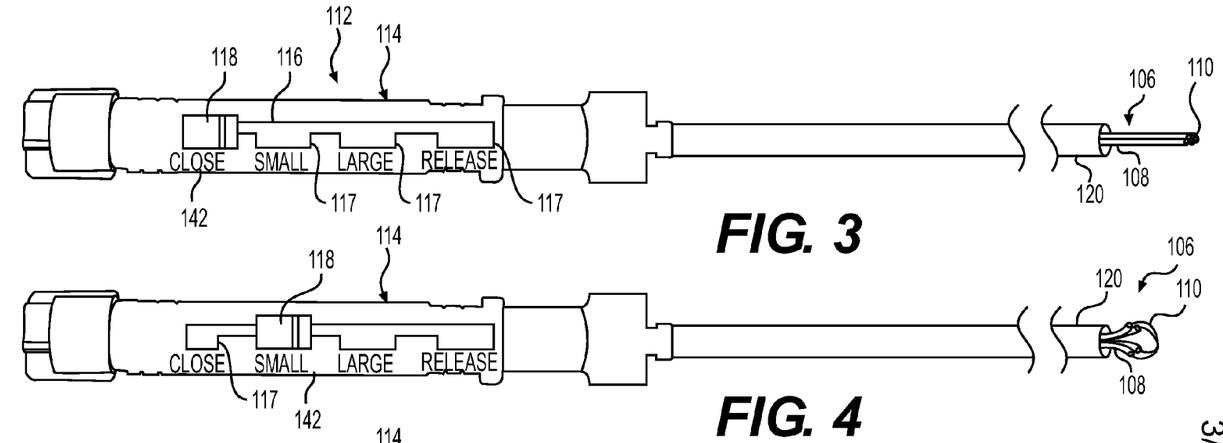
FIGS. 3-6 are a series of side view illustrations of the medical retrieval device of FIG. 1 from a closed configuration to a fully expanded configuration.

Referring to FIGS. 1 and 3-6, the actuation selector 118 may be configured to slide within handle 112 to exert or release a tensioning force, or exert or release a pushing force on the filament 110 to extend or retract the filament 110. This movement may also transition the branch members 108 between various distances to vary the size of the grasping portion 106. As shown in FIG. 3, distal portions of branch members 108 may be moved to parallel linear positions (e.g. a collapsed or "CLOSE" position) from expanded positions by displacing the actuation selector 118 along the actuation guide.

In a configuration where distal portions of the branch members 108 may be naturally radially biased away from the longitudinal axis 134, displacing the actuation selector 118 may require a tensioning or pulling force on the filament portions 110 connected to the distal ends of the branch members 108 so that the branch members 108 are forced radially inwards towards the longitudinal axis 134 and have a more collapsed configuration. In this example, the filament 110 may have sufficient strength and flexibility to transfer forces to the branch members 108.

Alternatively, in a configuration in which the distal ends of the branch members 108 are naturally linear and parallel to the longitudinal axis 134, displacement of the actuation selector 118 towards an open position along the actuation guide 116 may require a pushing force on the portions of the filament 110 connected to the distal ends of the branch members 108 so that the branch members 108 are forced radially from the longitudinal axis 134. In this example, the filament 110 may have sufficient columnar strength and flexibility to transfer forces to the branch members 108.

The actuation guide 116 may include a longitudinal slot with notches 117 extending from the slot. The actuation guide 116 may extend the entire length or a portion of the length of the handle 112 and may have any suitable size or shape. The handle 112 may be made using any suitable material, such as plastic or metal and may include various gripping features, such as indentations, surface patterns, coatings, sleeves, etc. The actuation guide 116 may be formed in the handle in any suitable manner, such mechanical or laser cutting, etc. The identifiers 142 may be made on the handle in any suitable manner, such as being embossed, engraved, printed, etc. The actuation selector 118 may having any suitable size and shape, and the exterior surface may include one or more surface features, including rubber coating, depressions, grooves, protrusions, etc., suitable for a user to push and/pull. The portion of the selector 118 may include various features for operatively coupling to the guide 116.

The two ends 122 and 124 of filament 110 may be operatively connected to the actuation selector 118. The connection between the actuation selector 118 and the ends 122, and 124 of the filament 110 may be operatively coupled via a direct or indirect connection (e.g. via a drive wire 182) and/or via any other suitable arrangement). The connection to the actuation selector 118 may be made in any suitable manner, such as a loop and hook, snap fit connection, glue, solder, knot, screw, etc.

In use, as the actuation selector 118 may be moved along the actuation guide 116, it may displace the filament 110 through the sheath member 120 and/or any other intervening portion of the device 100, and extend or retract portions of the filament 110 at the distal end of the branch members 108.

Figure 5:
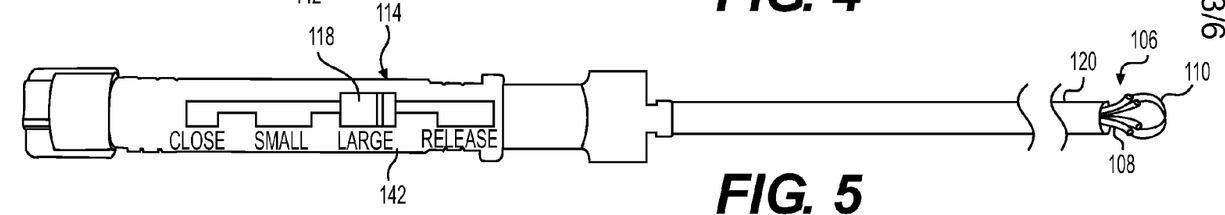
Figure 6:
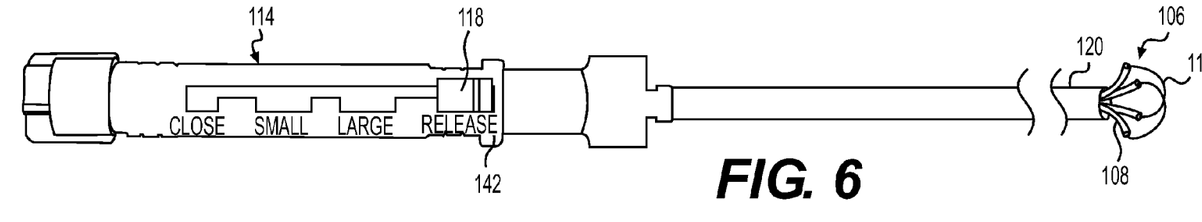

As shown in FIGS. 4-6, the grasping portion 106 may expand various degrees by the actuation selector 118 by exerting or releasing a force on the filament 110, which in turn may move the branch members 108 (or allow the branch members 108 to move) radially outward at their distal ends. In the examples described above, the branch members 108 may have sufficient flexibility and other properties to move orientations and positions, and the filament 110 may have sufficient flexibility and/or columnar strength and other suitable properties to transfer forces from the actuation selector 118 to the distal ends of the branch members 108 to move the branch members 108.

The branch members 108 may be positioned such that the grasping portion 106 may be oriented around a target site in the body, such as a kidney stone. The branch members 108 may be retracted from the open or expanded configuration by displacing the proximal ends of the filament 110, which may in turn vary the distance between each branch member 108.

In use, the actuation selector 118 may move along the guide 116 having identifiers 142 corresponding to the configuration of the grasping portion 106 at that position of the actuation selector 118, for example "CLOSE", "SMALL", "LARGE", and "RELEASE". The actuation selector 118 may be slidably housed in the handle 112 of the device 100 and the guide 116 may include notches 117 corresponding to each of the identified position into which the actuation selector 118 may be biased.

The filament 110 may deflect or move to create a greater opening between the filament portions 110 to allow body matter, such as concretions, to be encapsulated between the filament portions 110 and then gathered and captured by the branch members 108. With this type of closure, the grasping portion 106 may be closed from the distal end towards the proximal end rather than conventional method of closing a basket from the proximal end.

For example, the actuation selector 118 may be moved along the actuation guide 116 and into notches 117 with corresponding identifiers 142 identifying various configurations of the grasping portion 106, e.g. "CLOSE", "SMALL", "LARGE", and "RELEASE". The movement of the actuation selector 118 along the guide 116 and into the various notches 117 of the actuation guide 116 of the handle 112 may be used to extend or retract the portions of the filament 110 extending out of the distal apertures 136 of the branch members 108. For example, when the actuation selector 118 is moved from "CLOSE" to "SMALL", the actuation selector 118 displaces a predetermined filament length into the branch members 108 and forms a basket configuration having a pre-selected discrete configuration. This option may be used to capture body matter, which may enter the basket from spaces between adjacent branch members 108. In order to capture larger body matter, the actuation selector 118 may be displaced to "LARGE" to extend the length of the portions of the filament 110 extending from the distal opening 136 of the branch members 108. When body matter is gathered in the basket formed of portions of the filament 110, the actuation selector 118 may be displaced to the "CLOSE" position from the "SMALL" or "LARGE" positions, to capture the body matter, by retracting a predetermined amount of wire. This may close the basket formed of the portions of the filament 110 and surround the body matter with the branch members 108. The body matter may then be released, for example, by displacing the actuation selector 118 to the "RELEASE" position, which may extend a greater length of filament from the distal apertures 136 of the branch members 108 and allow the body matter to be released from the grasping portion 106.

The actuator 114 also may include identifiers 142 corresponding to grasping portion 106 positions to gauge the size of body matter based on predetermined discrete sizes of body matter. For example body matter (e.g. concretions) captured within a smaller size basket configuration may indicate that the body matter is too small to be directly removed from the body. In addition, body matter captured in larger sized baskets, and/or inability of the grasping portion 106 to close after capturing body matter may indicate that the body matter may need to be removed using another device or method (e.g. fragmentation).

Figure 7:
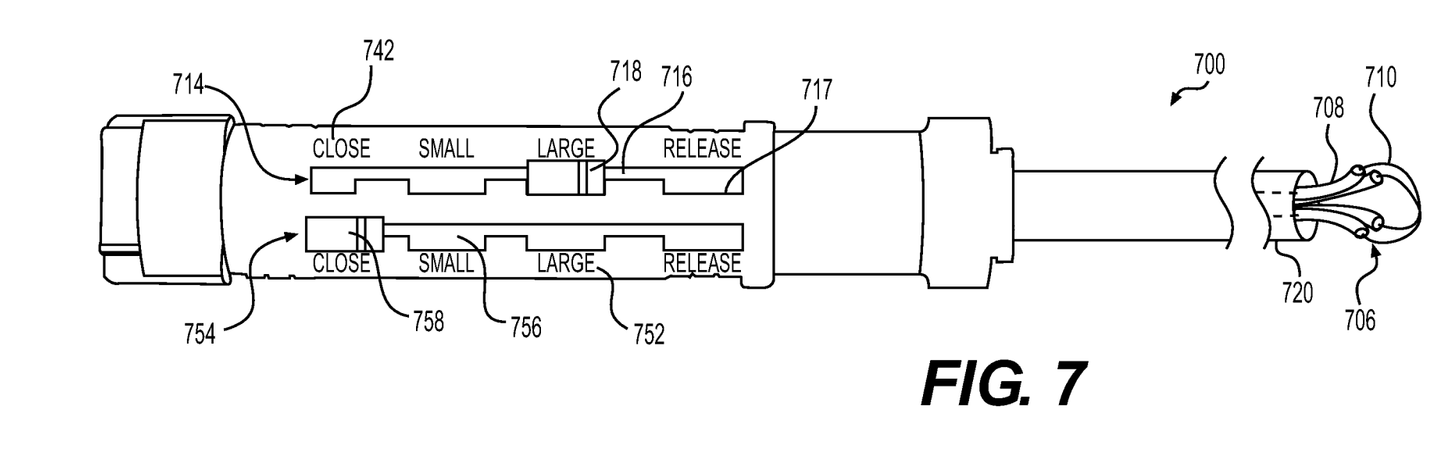
FIG. 7 is a side view illustration of a medical retrieval device in accordance with another embodiment of the present disclosure.

In FIGS. 1-6, the two ends 122 and 124 of the filament 110 are shown to connect to a single actuation selector 118. FIG. 7 shows a medical device 700 according to another exemplary embodiment of the present disclosure similar to medical device 100 in FIGS. 1-6, including a grasping portion 706 having branch members 708 a filament 710 with two ends 722 and 724, and a sheath member 720.

Medical device 700 includes two sets of actuators 714 and 754 each having an actuation selector 718, 758, guides 716, 756, identifiers 742, 752, and notches 717 and 757. Each actuation selector 718 and 758 may be connected to a different end 722 and 724 of the filament 710 either directly or via a drive wire in a similar manner as described above in reference to FIGS. 1-6. This may allow independent movement and manipulation of each end 722 and 724 of the filament 710 and different branch members 708. The two actuation selectors 718 and 758 may provide the same or different actuation forces, and may exert the same or different degrees of tension or pushing force.

In addition the identifiers 742 and 752 may be the same or different in each actuator 714 and 754. As shown in FIG. 7, the identifiers 742 and 752 are shown to be aligned; however, the identifiers 742 and 752 may be positioned in any suitable manner. One of the actuators 714 and 754 may allow finer manipulation of the grasping portion 106. For example, movement of the selector 714 may allow for manipulation of the grasper member 106 from "CLOSE", "SMALL", LARGE and "RELEASE" positions. In addition, movement of the other actuation selector 758 may provide finer manipulation of the grasper 106 between each of the "CLOSE", "SMALL", "LARGE and "RELEASE" positions by extending and retracting a predetermined smaller length of filament 710 than the predetermined amount used by the first selector 718. In addition, the use of two or more actuators may provide for more fixed positions and configurations of the grasping portion 106.

Figure 8:
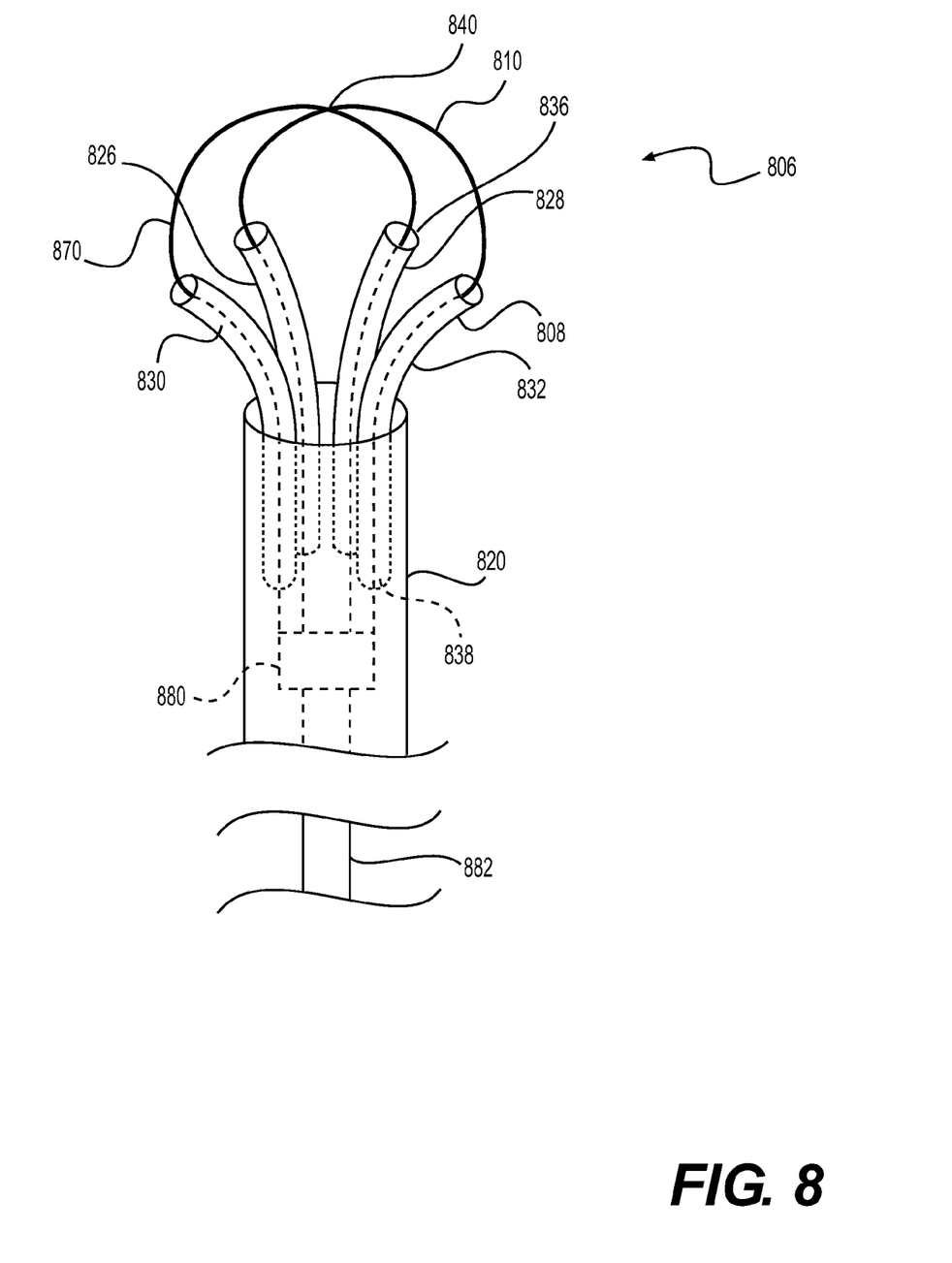
FIG. 8 is a partial side view illustration, of a distal portion of a medical retrieval device in an expanded configuration in accordance with another embodiment of the present disclosure.

FIG. 8 shows a grasping portion 806 at a distal end of a medical retrieval device according to another exemplary embodiment of the present disclosure. The grasping portion 806 may be similar to the grasping portion 106 of the medical device shown in FIGS. 1-6, including branch members 808, and sheath member 820, except, the grasping portion 806 may include two filaments 810 and 870, which may intersect at apex 840. In one embodiment the intersecting portions of the filaments 810 and 870 may be connected, e.g. via a knot, glue, solder, twisting etc. In another embodiment the intersecting portions of the filaments 810 and 870 may not be connected.

Each end 822 and 824 of a first filament 810 may enter a pair of branch members 826 and 830 via distal apertures 836 and each end 872 and 874 of a second filament 870 may enter another pair of branch members 828 and 832 via distal apertures 836. Each end of each filament 822, 824, 872, and 874 (e.g. four ends in total) may exit the lumen of the branch members 826, 828, 830, and 832 via proximal openings 838 and may be operatively coupled to the actuation selector via, for example, a drive wire 882 or by any other suitable manner.

In one embodiment, each end of the filaments 822, 824, 872, and 874 may be coupled to the drive wire 882 via a connector 880, such as a crimp, tying, or any other suitable manner. The drive wire 882 may be manufactured using any suitable material, such as a metal, or polymer having suitable properties to transfer forces from the actuator and may have any suitable dimensions.

Figure 9:
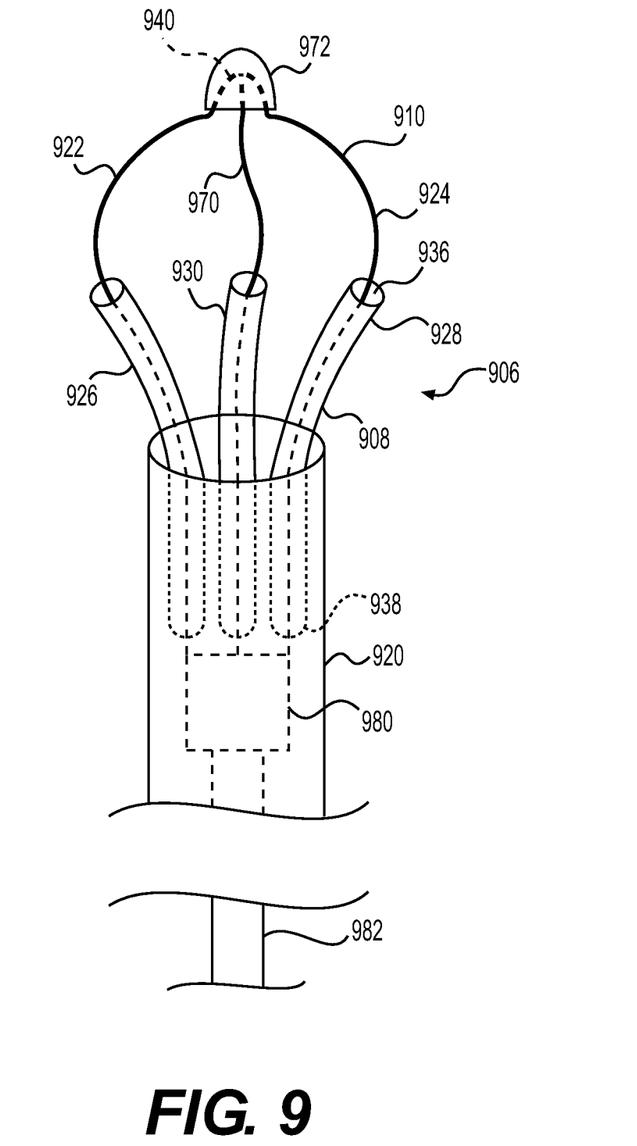
FIG. 9 is a partial side view illustration, of a distal portion of a medical retrieval device in an expanded configuration in accordance with another embodiment of the present disclosure.

FIG. 9 shows a grasping portion 906 at a distal end of a medical retrieval device according to another exemplary embodiment of the present disclosure. The grasping portion 906 may be similar to the grasping portion 106 of the medical device shown in FIGS. 1-6, including branch members 908, and sheath member 920, except, the grasping portion 906 may include three branch members 926, 928, 930, and two filaments 910 and 970, which may intersect at an apex 940. The intersecting portions of the filaments 910 and 970 may form a connection at the apex 940, e.g. via a bullet crimp knot, glue, solder, cap, twisting etc. Each end 922 and 924 of filament 910 may enter a pair of branch members 926 and 928 via distal apertures 936, and filament 970 may enter branch member 930 via a single distal aperture 936. Each end of each filament 922, 924, 970, (e.g. three ends in total) may exit the lumen of the branch members 926, 928, and 930 via proximal openings 938 and be connected at 980 in any other suitable manner, such as via a crimp, glue, solder, etc., and connected to one or more actuation selectors via a drive wire 982, or in any other suitable manner. In other similar embodiments, the grasping portion may include any other odd number of branch members (e.g. 5, 7, 9), each having a filament which enters only one branch member.

In the expanded configuration, a user may manipulate medical devices disclosed herein to capture materials within a patient, such as, e.g., a kidney stone, biliary stone, tissue, or the like. Any aspect set forth in any embodiment may be used with any other embodiment set forth herein. Every device and apparatus set forth herein may be used in any suitable medical procedure, may be advanced through any suitable body lumen and body cavity, and may be used to remove material from any suitable body portion. For example, the apparatuses and methods described herein may be used through any natural body lumen or tract, including those accessed orally, vaginally, rectally, nasally, urethrally, or through incisions in any suitable tissue. The device described in this disclosure achieves a small profile having with few moving parts and joints and provides varying sizes and configurations for capture, release, and gauging of body matter.

In some embodiments, the filaments, such as filaments 110, may have a coil shape (not shown), and/or include coil shaped components over the filaments to enhance grip and assist in deployment of the basket. In some embodiments, the handle indicator 142 may be configured to include a continuous movement and lock so that the size of the basket can move from closed to large or release positions with any number of steps. This may be achieved using any suitable mechanism, for example, with a rack and pinion, and/or with a friction-fitting portion of the handle 112 moving within the handle 112 housing. Other locking mechanisms may include thumbscrews or spring-loaded buttons—disengaged to move the basket, and engaged to lock basket. In some embodiments, the distal end of the basket may be configured to open so as to grasp objects. In some embodiments, there may be more than two loops.

In some embodiments, the handle 112 may be spring loaded to allow the basket to expand (or contract depending on spring direction) to the next staged size.

It will be apparent to those skilled in the art that various modifications and variations can be made in the disclosed systems and processes without departing from the scope of the invention. For example, two, three, or more than four branch members may be used in the medical retrieval device. Wherein in systems with an odd number of branch members, a filament may enter through a plurality of branch members one or more times. Other embodiments of the invention will be apparent to those skilled in the art from consideration of the specification and practice of the invention disclosed herein. It is intended that the specification and examples be considered as exemplary only. The following disclosure identifies some other exemplary embodiments.

We claim:

1. A medical device, comprising:
   a distal end including an expandable grasping portion having a plurality of movable branch members having a lumen, and a continuous filament member connected to and slidably movable within at least a portion of the plurality movable branch members;
   a proximal end including a handle having at least two actuation guides and at least two actuation selectors each connected to and movable along one of the at least two actuation guides, wherein the at least two actuation selectors are connected to ends of the continuous filament member in the proximal end of the medical device, and wherein the at least two actuation selectors are movable to vary the size of the grasping portion between a plurality of pre-selected, discrete configurations of the grasping portion; and
   a sheath member extending from the distal end toward the proximal end, wherein proximal ends of the plurality of movable branch members are disposed within the sheath member,
   wherein the plurality of movable branch members includes at least a first branch member, a second branch member, a third branch member, and a fourth branch member, with each of the branch members having a distal aperture and a proximal aperture, wherein one end of the one continuous filament member passes through the proximal aperture of a first branch member, out of the distal aperture of the first branch member, into the distal aperture of the third branch member, and out of the proximal aperture of the third branch member, and wherein a second end of the continuous filament member passes through the proximal aperture of the second branch member, out of the distal aperture of the second branch member, into the distal aperture of the fourth branch member, and out of the proximal aperture of the fourth branch member.

2. The medical device of claim 1, wherein the filament member is a single filament having portions extending through the lumen of each of the plurality of branch members and coupled to the actuation selector.

3. The medical device of claim 1, wherein each branch member is pre-bent to extend radially from a longitudinal axis when a force is not applied to the plurality of movable branch members.

4. The medical device of claim 1, wherein a distal portion of each of the plurality movable branch members has a linear neutral position when a force is not applied to the plurality of movable branch members.

5. The medical device of claim 1, wherein distal portions of the filament member extend from distal apertures of the plurality of movable branch members and intersect at an apex.

6. The medical device of claim 5, wherein the distal portions of the filament member intersecting at the apex are connected to each other.

7. The medical device of claim 6, wherein the distal portions of the filament member intersecting at the apex and connected to each other are connected via a knot.

8. The medical device of claim 1, wherein the at least two actuation selectors have a first position relative to the actuation guide and a second position relative to the actuation guide, the second position being different than the first position, wherein the filament member extends distally of the plurality of moveable members to a greater extent when the actuation guide is in the first position than in the second position.

9. The medical device of claim 1, wherein the at least two actuation guides comprise notches each corresponding to a discrete configuration of the grasping portion.

10. The medical device of claim 9, wherein the notches further correspond to a pre-determined degree of extension of the filament member relative to the plurality of moveable members.

11. The medical device of claim 9, wherein the notches further correspond to a pre-determined degree of extension of the filament relative to the plurality of moveable members.

12. The medical device of claim 1, wherein the at least two actuation guides include identifiers for the plurality of pre-selected, discrete configurations at the grasping portion.

13. The medical device of claim 1, wherein the plurality of moveable branch members are moveable relative to the sheath.

14. The medical device of claim 1, wherein distal portions of the filament member extend from distal apertures of the plurality of movable branch members and intersect at an apex, wherein the distal portions of the filament member intersecting at the apex are connected to each other via a knot.

* * * * *